United States Patent
Marous, III et al.

(10) Patent No.: US 12,318,521 B2
(45) Date of Patent: *Jun. 3, 2025

(54) VA ECMO WITH PULMONARY ARTERY VENTILATION

(71) Applicant: CardiacAssist, Inc., Pittsburgh, PA (US)

(72) Inventors: John C. Marous, III, Pittsburgh, PA (US); Robert G. Svitek, Freeport, PA (US); Jerry Stokes, Sarver, PA (US); Patrick A. Kelly, North Huntingdon, PA (US)

(73) Assignee: CardiacAssist, Inc.

( * ) Notice: Subject to any disclaimer, the term of this patent is extended or adjusted under 35 U.S.C. 154(b) by 1491 days.

This patent is subject to a terminal disclaimer.

(21) Appl. No.: 16/810,456

(22) Filed: Mar. 5, 2020

(65) Prior Publication Data

US 2020/0230308 A1 Jul. 23, 2020

Related U.S. Application Data

(63) Continuation of application No. 15/516,453, filed as application No. PCT/US2015/053781 on Oct. 2, 2015, now Pat. No. 10,603,422.

(Continued)

(51) Int. Cl.
*A61M 1/16* (2006.01)
*A61M 1/26* (2006.01)
(Continued)

(52) U.S. Cl.
CPC .......... *A61M 1/1698* (2013.01); *A61M 1/267* (2014.02); *A61M 1/3659* (2014.02);
(Continued)

(58) Field of Classification Search
CPC .. A61M 1/1698; A61M 1/267; A61M 1/3659; A61M 1/3667; A61M 1/3666;
(Continued)

(56) References Cited

U.S. PATENT DOCUMENTS 6,641,558 B1 11/2003 Aboul-Hosn
6,692,473 B2 * 2/2004 St. Cyr ............... A61M 1/3653
604/264

(Continued)

FOREIGN PATENT DOCUMENTS

DE 19947907 A1 4/2001
EP 1374930 A1 1/2004
(Continued)

*Primary Examiner* — Philip R Wiest
(74) *Attorney, Agent, or Firm* — Seager, Tufte & Wickhem LLP

(57) ABSTRACT

A veno-arterial extracorporeal membrane oxygenation system includes a dual lumen drainage cannula configured for withdrawing blood from a patient's vasculature in a manner that provides a perfusion of oxygenated blood with reduced carbon dioxide content while unloading the left ventricle, with two points of access to the patient's vasculature. The dual lumen drainage cannula has a first drainage tube and a second drainage tube co-axially aligned with the first drainage tube. The first and second drainage tubes are fluidly coupled to a connector. A blood pump having a pump inlet is configured for fluidly connecting with the connector, while an oxygenator having an oxygenator inlet is configured for fluidly connecting with a pump outlet. An infusion cannula is configured for fluidly connecting with an oxygenator outlet for infusing oxygenated blood into a patient's bloodstream.

15 Claims, 8 Drawing Sheets

Related U.S. Application Data

(60) Provisional application No. 62/059,033, filed on Oct. 2, 2014.

(51) Int. Cl.
*A61M 1/36* (2006.01)
*A61M 60/113* (2021.01)
*A61M 60/232* (2021.01)
*A61M 60/237* (2021.01)
*A61M 60/279* (2021.01)
*A61M 60/31* (2021.01)
*A61M 60/38* (2021.01)
*A61M 60/515* (2021.01)
*A61M 60/531* (2021.01)
*A61M 25/00* (2006.01)

(52) U.S. Cl.
CPC ........ *A61M 1/3666* (2013.01); *A61M 1/3667* (2014.02); *A61M 60/113* (2021.01); *A61M 60/232* (2021.01); *A61M 60/237* (2021.01); *A61M 60/279* (2021.01); *A61M 60/31* (2021.01); *A61M 60/38* (2021.01); *A61M 60/515* (2021.01); *A61M 60/531* (2021.01); *A61M 2025/0031* (2013.01)

(58) Field of Classification Search
CPC ........ A61M 2025/0031; A61M 60/232; A61M 60/537; A61M 60/237; A61M 60/279; A61M 60/38
See application file for complete search history.

(56) References Cited

U.S. PATENT DOCUMENTS

| | | | |
|---|---|---|---|
| 6,808,508 | B1 | 10/2004 | Zafirelis et al. |
| 7,090,659 | B2 * | 8/2006 | Aboul-Hosn ....... A61M 1/3666 604/8 |
| 7,473,239 | B2 | 1/2009 | Wang et al. |
| 7,785,246 | B2 * | 8/2010 | Aboul-Hosn ....... A61M 1/3621 600/16 |
| 8,562,519 | B2 * | 10/2013 | Smith ................ A61M 60/38 600/160 |
| 9,168,352 | B2 | 10/2015 | Kelly |
| 10,603,422 | B2 * | 3/2020 | Marous, III ........ A61M 60/845 |
| 2003/0040736 | A1 | 2/2003 | Stevens et al. |
| 2005/0085761 | A1 * | 4/2005 | Wang ................ A61M 25/0029 604/4.01 |
| 2005/0279370 | A1 * | 12/2005 | Aboul-Hosn ....... A61M 1/3659 604/9 |
| 2006/0270890 | A1 | 11/2006 | Viole et al. |
| 2009/0005725 | A1 * | 1/2009 | Shorey ............. A61M 25/005 29/525.01 |
| 2009/0069792 | A1 * | 3/2009 | Frey ................. A61M 1/3661 264/261 |
| 2013/0158338 | A1 * | 6/2013 | Kelly ............... A61M 60/13 600/16 |

FOREIGN PATENT DOCUMENTS

| | | |
|---|---|---|
| JP | 9509074 A | 9/1997 |
| WO | 9515192 A1 | 6/1995 |
| WO | 2016161114 A1 | 10/2016 |

* cited by examiner

VA ECMO WITH PULMONARY ARTERY VENTILATION

CROSS-REFERENCE TO RELATED APPLICATIONS

This application is a continuation of U.S. patent application Ser. No. 15/516,453, filed Apr. 3, 2017, which is a national phase of International Application No. PCT/US2015/053781 filed Oct. 2, 2015, which claims priority to U.S. Provisional Patent Application No. 62/059,033 filed Oct. 2, 2014, the disclosures of which are hereby incorporated in their entirety by reference.

BACKGROUND OF THE INVENTION

Field of the Invention

The present invention relates, in general, to devices and methods for assisting a patient's heart and/or lungs, with a cannula, a pump, and a gas exchange device. More specifically, the present invention relates to devices and methods for providing the patient with blood flow, oxygenation, and carbon dioxide removal, all while unloading the left side of the patient's heart with one cannula configured for draining blood flow from two sites within the patient's vasculature and a second cannula for returning blood into the patient's vasculature after gas exchange, with a pump and gas exchange device provided outside the patient's body.

Description of the Related Art

Traditional veno-arterial extracorporeal membrane oxygenation (VA ECMO) is the current standard of care used for treating right ventricular failure and respiratory failure percutaneously. A VA ECMO procedure draws blood from the right atrium and pumps it through an oxygenator and back into the arterial circulation via the femoral artery. VA ECMO bypasses the lungs and the heart completely, elevating arterial pressure and infusing blood into the arterial system with added oxygen and reduced carbon dioxide. One of the results of this therapy is that the blood that remains in the heart must be pumped by the heart to a higher pressure level in order to be ejected by the left ventricle because the VA ECMO system has elevated the arterial pressure to a higher level that represents a higher afterload to the pumping effort of the left ventricle.

In traditional VA ECMO systems, one cannula is placed in the right atrium to drain blood therefrom and a separate, second cannula is placed in an artery to return oxygenated (and cleansed from carbon dioxide) blood at a higher pressure. Some blood inevitably flows past the right atrium drainage cannula, and once the blood gets into the right ventricle, the heart's valves prevent this blood from being drained into the VA ECMO system. Instead, the blood flows into the left ventricle, which must pump this blood to the higher pressure of the arterial system. This causes an additional load on the heart. In patients with a severely weakened heart muscle, the left ventricle cannot pump the blood to the higher pressure of the arterial system, causing the left ventricle to be distended and requiring emergent action. Even in patients whose left ventricle is capable of pumping blood therefrom, fluid can build up in the patient's lungs. In both cases, surgery is generally required to (a) insert a second drainage cannula into the pulmonary artery, (b) implant a pump to operate along with the ECMO circuit; or (c) insert a transseptal cannula into the left atrium.

In the case of left ventricles being distended, emergency action is needed to get a cannula into the left ventricle to drain it and prevent it from continual expansion. This emergency action is either surgery or use of additional devices, with additional cost and with additional access site needs that involve bleeding and other complications. In the case of fluid buildup in the lungs without excessive left ventricular distension, the pulmonary fluid buildup can cause damage to the lungs if not treated with the expensive and/or invasive treatments. The surgery or additional device usage is to insert a cannula into the pulmonary artery or the left ventricle or the left atrium.

One of the major deficiencies of traditional VA ECMO systems and methods is that they do not sufficiently unload the heart and reduce the workload on the strained muscle. In one existing VA ECMO system, one drainage cannula is configured to draw blood from the right atrium, while a separate, second cannula is configured to draw blood from the pulmonary artery. The pulmonary artery cannula drains blood flowing past the right atrial drainage cannula, and it may also drain residual blood in the left atrium, thereby reducing left atrial pressure and thus preventing additional load on the heart, or resulting in VA ECMO with an unloaded left ventricle. Blood is drawn from both cannulas, pumped through an oxygenator and delivered back into the arterial circulation via a separate, third cannula into the femoral artery or the subclavian artery.

There are a number of disadvantages associated with traditional VA ECMO systems and the methods. Traditional cannulas used in VA ECMO procedures have a single lumen and are inserted at multiple insertion sites. Multiple insertion sites increase the risk of bleeding, vessel damage, and infection, as well as pain and discomfort to the patient. Moreover, these cannulas are designed and built for short-term acute therapies. While multi-lumen cannulas exist in the art, such cannulas are generally not configured for draining blood flow from two separate sites. For example, a dual lumen cannula, such as the dual lumen cannula described in US 2013/0158338, which is incorporated by reference herein in its entirety, can be used to unload the right side of the heart by drawing blood from the right atrium through one lumen and infusing blood to the pulmonary artery through a second lumen.

SUMMARY OF THE INVENTION

In view of the foregoing, there is a need for a VA ECMO system and method having a multi-lumen drainage cannula with a single insertion point. There is an additional need for a VA ECMO system and method having a multi-lumen drainage cannula that eliminates multiple access sites and reduces bleeding, vessel damage, and infection, as well as pain and discomfort to the patient. Furthermore, there exists a need for a VA ECMO system and method having a multi-lumen drainage cannula that enables patients to be ambulatory with access sites provided in the neck or groin area.

According to one aspect of the present disclosure, a VA ECMO system may include a dual lumen drainage cannula having a first drainage tube with a proximal end, a distal end, and a sidewall extending between the proximal end and the distal end. The dual lumen cannula may further have a second drainage tube coaxially aligned with the first drainage tube with a proximal end, a distal end, and a sidewall extending between the proximal end and the distal end. A connector may be configured for fluidly connecting with the first drainage tube and the second drainage tube. The VA ECMO system may further have a blood pump with a pump inlet and a pump outlet. The pump outlet may be configured for fluidly connecting to the connector. The VA ECMO system may further have an oxygenator having an oxygenator inlet and an oxygenator outlet. The oxygenator inlet may be configured for fluidly connecting with the pump outlet; and an infusion cannula configured for fluidly connecting with the oxygenator outlet.

According to another aspect of the present disclosure, the first drainage tube may have at least one first drainage aperture provided at the distal end. The second drainage tube may have at least one second drainage aperture provided at the distal end. The at least one first drainage aperture may extend through the sidewall of the first drainage tube. The at least one second drainage aperture may extend through the sidewall of the second drainage tube. The at least one first drainage aperture may extend through the sidewall of the first drainage tube in a direction perpendicular to a longitudinal axis of the first drainage tube. The at least one second drainage aperture may extend through the sidewall of the second drainage tube in a direction perpendicular to a longitudinal axis of the second drainage tube. The at least one first drainage aperture may extend through the sidewall of the first drainage tube at an acute or obtuse angle with respect to a longitudinal axis of the first drainage tube. The at least one second drainage aperture may extend through the sidewall of the second drainage tube at an acute or obtuse angle with respect to a longitudinal axis of the second drainage tube. A plurality of first drainage apertures may extend in a circular pattern around the first drainage tube. A plurality of second drainage apertures may extend in a circular pattern around the second drainage tube. The at least one first drainage aperture may be separated from the at least one second drainage aperture by a predetermined distance along a longitudinal axis of the first drainage tube. The predetermined distance may be selected based on at least one of patient age, patient size, and a desired flow rate. The dual lumen cannula may be adapted for maneuvering through the patient's vasculature such that the distal end of the first drainage tube is substantially within the patient's right atrium and such that the distal end of the second drainage tube is substantially within the patient's pulmonary artery. The pump may be a centrifugal pump, an axial pump, or a roller pump. A controller may be provided for controlling the operation of the pump.

According to another aspect of the present disclosure, a dual lumen drainage cannula may be configured for use in a VA ECMO system. The dual drainage cannula may have a first drainage tube configured for insertion into a right atrium of a patient and a second drainage tube configured for insertion into a pulmonary artery of a patient. The first drainage tube may have a body with a proximal end, a distal end, and a sidewall extending between the proximal end and the distal end with at least one first drainage aperture provided at the distal end. The at least one first drainage aperture may extend through the sidewall of the first drainage tube. The second drainage tube may be coaxially aligned with the first drainage tube and may have a proximal end, a distal end, and a sidewall extending between the proximal end and the distal end with at least one second drainage aperture provided at the distal end. The at least one second drainage aperture may extend through the sidewall of the second drainage tube. The dual lumen drainage cannula may have a connector configured for fluidly connecting with the first drainage tube and the second drainage tube. The at least one first drainage aperture may be separated from the at least one second drainage aperture by a predetermined distance along a longitudinal axis of the first drainage tube. The predetermined distance may be selected based on at least one of patient age, patient size, and a desired flow rate.

According to another aspect of the present disclosure, a method of providing VA ECMO of a heart may include providing a dual lumen drainage cannula having a first drainage tube with a body with a proximal end, a distal end, and a sidewall extending between the proximal end and the distal end with at least one first drainage aperture provided at the distal end. The at least one first drainage aperture may extend through the sidewall of the first drainage tube. The dual lumen drainage cannula may further have a second drainage tube coaxially aligned with the first drainage tube and may have a proximal end, a distal end, and a sidewall extending between the proximal end and the distal end with at least one second drainage aperture provided at the distal end. The at least one second drainage aperture may extend through the sidewall of the second drainage tube. The dual lumen drainage cannula may further have a connector configured for fluidly connecting with the first drainage tube and the second drainage tube. The method may further include inserting the dual lumen drainage cannula into a first site in a patient's vasculature, maneuvering the dual lumen drainage cannula through the patient's vasculature such that the first distal end of the first infusion tube is at least within proximity of the patient's right atrium and such that the second distal end of the second drainage tube is at least within proximity of the patient's pulmonary artery, withdrawing blood through the first and second drainage tubes using a blood pump, pumping withdrawn blood through an oxygenator to reduce carbon dioxide content of the blood, and delivering oxygenated blood with reduced carbon dioxide content to a second site in the patient's vasculature.

In accordance with other aspects of the present disclosure, the VA ECMO system and method may be characterized by one or more of the following clauses:

Clause 1. A VA ECMO system comprising: a dual lumen drainage cannula comprising: a first drainage tube having a proximal end, a distal end, and a sidewall extending between the proximal end and the distal end; a second drainage tube coaxially aligned with the first drainage tube and having a proximal end, a distal end, and a sidewall extending between the proximal end and the distal end; and a connector configured for fluidly connecting with the first drainage tube and the second drainage tube; a blood pump having a pump inlet and a pump outlet, the pump outlet configured for fluidly connecting to the connector, an oxygenator having an oxygenator inlet and an oxygenator outlet, the oxygenator inlet configured for fluidly connecting with the pump outlet; and an infusion cannula configured for fluidly connecting with the oxygenator outlet.

Clause 2. The VA ECMO system according to clause 1, wherein the first drainage tube has at least one first drainage aperture provided at the distal end.

Clause 3. The VA ECMO system according to clause 1 or 2, wherein the second drainage tube has at least one second drainage aperture provided at the distal end.

Clause 4. The VA ECMO system according to any of clauses 2-3, wherein the at least one first drainage aperture extends through the sidewall of the first drainage tube.

Clause 5. The VA ECMO system of according to any of clauses 3-4, wherein the at least one second drainage aperture extends through the sidewall of the second drainage tube.

Clause 6. The VA ECMO system according to any of clauses 2-5, wherein the at least one first drainage aperture extends through the sidewall of the first drainage tube in a direction perpendicular to a longitudinal axis of the first drainage tube.

Clause 7. The VA ECMO system according to any of clauses 3-6, wherein the at least one second drainage aperture extends through the sidewall of the second drainage tube in a direction perpendicular to a longitudinal axis of the second drainage tube.

Clause 8. The VA ECMO system according to any of clauses 2-7, wherein the at least one first drainage aperture extends through the sidewall of the first drainage tube at an acute or obtuse angle with respect to a longitudinal axis of the first drainage tube.

Clause 9. The VA ECMO system according to any of clauses 3-8, wherein the at least one second drainage aperture extends through the sidewall of the second drainage tube at an acute or obtuse angle with respect to a longitudinal axis of the second drainage tube.

Clause 10. The VA ECMO system according to any of clauses 2-9, wherein a plurality of first drainage apertures extends in a circular pattern around the first drainage tube.

Clause 11. The VA ECMO system according to any of clauses 3-10, wherein a plurality of second drainage apertures extends in a circular pattern around the second drainage tube.

Clause 12. The VA ECMO system according to any of clauses 3-11, wherein the at least one first drainage aperture is separated from the at least one second drainage aperture by a predetermined distance along a longitudinal axis of the first drainage tube.

Clause 13. The VA ECMO system according to clause 12, wherein the predetermined distance is selected based on at least one of patient age, patient size, and a desired flow rate.

Clause 14. The VA ECMO system according to any of clauses 1-13, wherein the dual lumen cannula is adapted for maneuvering through the patient's vasculature such that the distal end of the first drainage tube is substantially within the patient's right atrium and such that the distal end of the second drainage tube is substantially within the patient's pulmonary artery.

Clause 15. The VA ECMO system according to any of clauses 1-14, wherein the pump is a centrifugal pump, an axial pump, or a roller pump.

Clause 16. The VA ECMO system according to any of clauses 1-15, further comprising a controller for controlling the operation of the pump.

Clause 17. A dual lumen drainage cannula configured for use in a VA ECMO system, the dual drainage cannula comprising: a first drainage tube configured for insertion into a right atrium of a patient, the first drainage tube having a body with a proximal end, a distal end, and a sidewall extending between the proximal end and the distal end with at least one first drainage aperture provided at the distal end, the at least one first drainage aperture extending through the sidewall of the first drainage tube; a second drainage tube configured for insertion into a pulmonary artery of a patient, the second drainage tube coaxially aligned with the first drainage tube and having a proximal end, a distal end, and a sidewall extending between the proximal end and the distal end with at least one second drainage aperture provided at the distal end, the at least one second drainage aperture extending through the sidewall of the second drainage tube; and a connector configured for fluidly connecting with the first drainage tube and the second drainage tube.

Clause 18. The VA ECMO system of clause 17, wherein the at least one first drainage aperture is separated from the at least one second drainage aperture by a predetermined distance along a longitudinal axis of the first drainage tube.

Clause 19. The VA ECMO system of clause 18, wherein the predetermined distance is selected based on at least one of patient age, patient size, and a desired flow rate.

Clause 20. A method of providing VA ECMO of a heart, the method comprising: providing a dual lumen drainage cannula comprising: a first drainage tube having a body with a proximal end, a distal end, and a sidewall extending between the proximal end and the distal end with at least one first drainage aperture provided at the distal end, the at least one first drainage aperture extending through the sidewall of the first drainage tube; a second drainage tube coaxially aligned with the first drainage tube and having a proximal end, a distal end, and a sidewall extending between the proximal end and the distal end with at least one second drainage aperture provided at the distal end, the at least one second drainage aperture extending through the sidewall of the second drainage tube; and a connector configured for fluidly connecting with the first drainage tube and the second drainage tube; inserting the dual lumen drainage cannula into a first site in a patient's vasculature; maneuvering the dual lumen drainage cannula through the patient's vasculature such that the first distal end of the first infusion tube is at least within proximity of the patient's right atrium and such that the second distal end of the second drainage tube is at least within proximity of the patient's pulmonary artery; withdrawing blood through the first and second drainage tubes using a blood pump; pumping withdrawn blood through an oxygenator to reduce carbon dioxide content of the blood; and delivering oxygenated blood with reduced carbon dioxide content to a second site in the patient's vasculature.

These and other features and characteristics of the VA ECMO system having a multi-lumen drainage cannula, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION OF THE INVENTION

Figure 1:
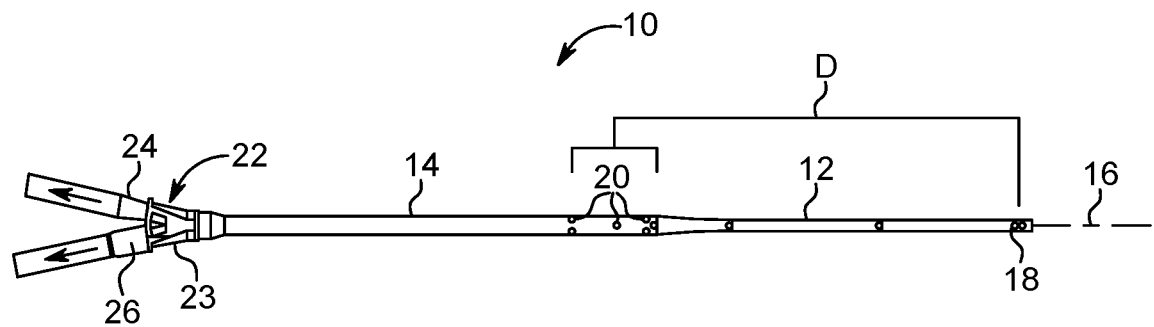
FIG. 1 is a top view of one aspect of a drainage cannula shown with a connector.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to the syringe, the term "proximal" refers to the portion of a cannula closer to a medical practitioner handling a cannula. The term "distal" refers to a portion of a cannula farther from a medical practitioner handling ae cannula. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Figure 10:
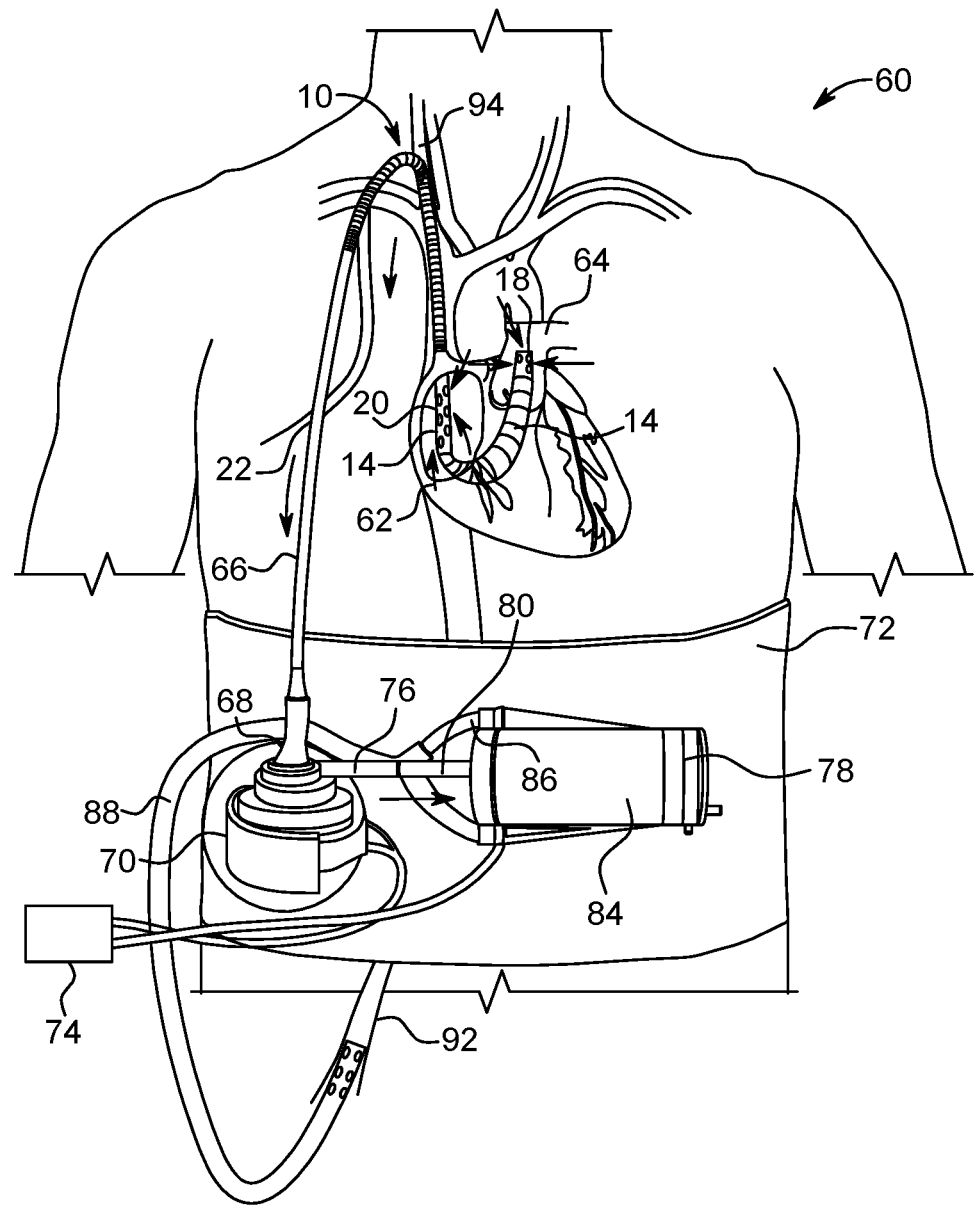
FIG. 10 is an illustration of a VA ECMO system in accordance with another aspect.
Figure 11:
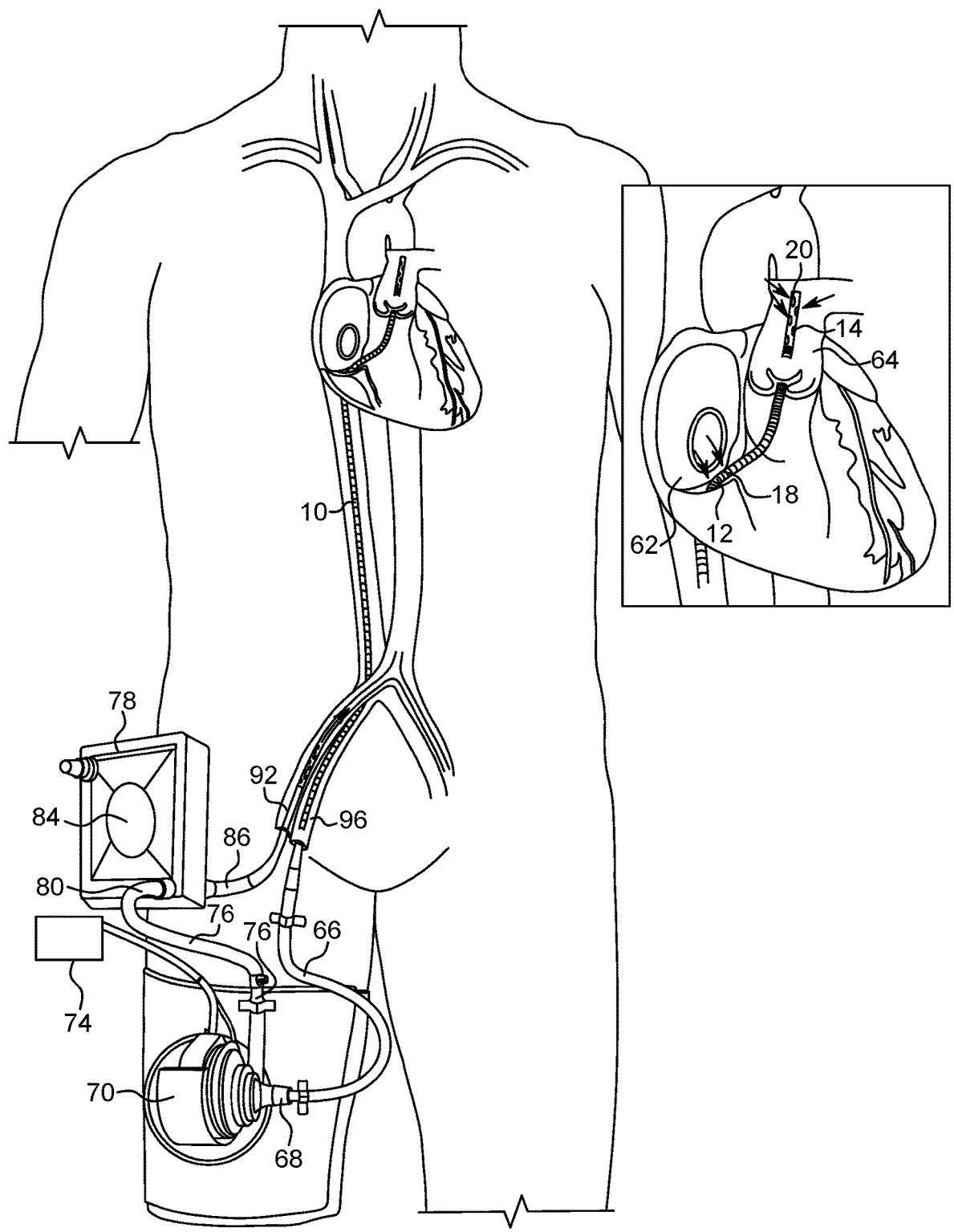
FIG. 11 is an illustration of a VA ECMO system in accordance with another aspect.

Referring to the drawings, in which like reference characters refer to like parts throughout the several views thereof; various aspects of a VA ECMO system and method will be discussed with reference to FIGS. 9-11. In various aspects, the VA ECMO system and method discussed herein utilize a multi-lumen drainage cannula. In some non-limiting aspects, a coaxial, dual lumen drainage cannula 10 (hereinafter referred to as "drainage cannula 10") is shown. With initial reference to FIGS. 1-2, an assembled drainage cannula 10, according to one aspect, generally includes a first drainage tube 12 having a first length and a second drainage tube 14 having a second length. In some aspects, the first length of the first drainage tube 12 is greater than the second length of the second drainage tube 14.

The first drainage tube 12 is disposed within the second drainage tube 14 in a coaxial arrangement centered about a central axis 16. In other aspects, the first and second drainage tubes 12, 14 may be arranged in a side-by-side arrangement with an axial alignment of the tubes 12, 14 along the length thereof. Each of the first drainage tube 12 and the second drainage tube 14 has a first circumference defining a first lumen and a second circumference defining a second lumen, respectively. The first circumference of the first drainage tube 12 is smaller than the second circumference of the second drainage tube 14 such that the first drainage tube 12 may be placed within the second lumen of the second drainage tube 14. One or both of the first drainage tube 12 and the second drainage tube 14 may be manufactured from a medical-grade material, such as polyurethane. Alternatively, one or both of the first drainage tube 12 and the second drainage tube 14 may be made from PVC or silicone, and may be dip molded, extruded, co-molded, or made using any other suitable manufacturing technique.

The drainage cannula 10 has sufficient placement flexibility adapted for placement of the drainage cannula 10 within a patient's body. The drainage cannula 10 may be used with an introducer (not shown) to guide the drainage cannula 10 as it is inserted within the patient's body.

Figure 2:
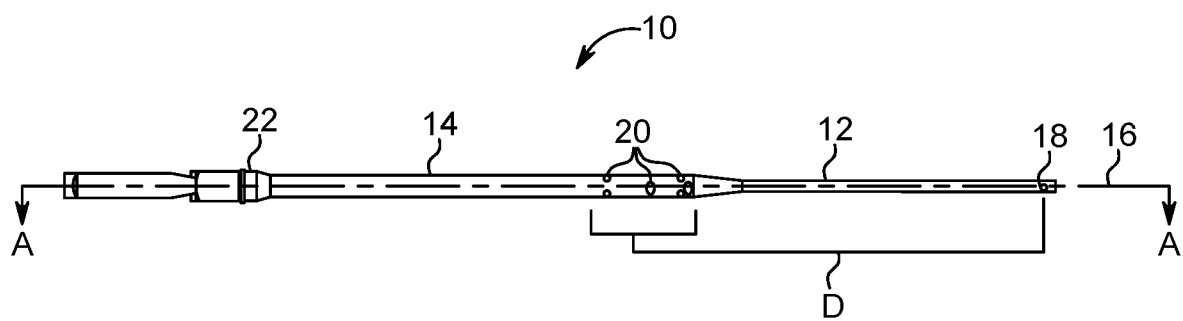
FIG. 2 is a side view of the drainage cannula shown in FIG. 1.

Desirably, a vascular insertion site is provided at the internal jugular vein on the patient's neck area or the femoral vein on the patient's groin area. The drainage cannula 10 is adapted for placement above or below the right atrium of the patient's heart with an access to the patient's pulmonary artery. With continuing reference to FIGS. 1-2, the drainage cannula 10 is configured to withdraw blood directly from the patient's heart. Withdrawn blood is returned back into the patient's heart via an infusion cannula after oxygenating the blood within an oxygenator, as described herein. In some aspects, the first drainage tube 12 is configured for positioning within the patient's pulmonary artery to draw blood therefrom, while the second drainage tube 14 is configured for positioning within the patient's right atrium to draw blood therefrom.

A plurality of first drainage apertures 18 is provided at a distal end of the first drainage tube 12. In one aspect, the plurality of first drainage apertures 18 may be arranged in a circular pattern extending around an outer circumference of the first drainage tube 12. In some aspects, the plurality of first drainage apertures 18 may be disposed in multiple groups provided at various sites along an axial length of the first drainage tube 12. Similarly, the second drainage tube 14 includes a plurality of second drainage apertures 20 provided at a distal end of the second drainage tube 14. In one aspect, the plurality of second drainage apertures 20 may be arranged in a circular pattern extending around an outer circumference of the second drainage tube 14. In other aspects, the plurality of second drainage apertures 20 may be arranged in groups disposed at various sites along an axial length of the second drainage tube 14. The first drainage apertures 18 are separated from the second drainage apertures 20 by a distance D in an axial direction along the length of the drainage cannula 10. In different aspects of the drainage cannula 10, the axial separation of the first drainage apertures 18 from the second drainage apertures 20 is based on a distance between the pulmonary artery and the right atrium of the patient. This distance may vary based on the age and size of the patient. For example, a drainage cannula 10 having a specific overall length and diameter, along with a desired pattern and distance between the first drainage apertures 18 and the second drainage apertures 20 may be selected based on age and/or size of the patient.

With continuing reference to FIGS. 1-2, a connector 22 is provided at the proximal end of the drainage cannula 10. The connector 22 includes a first outlet portion 23 in fluid communication with the first drainage tube 12 to transfer blood from the first drainage tube 12 to a blood pump in the direction of the arrow shown in FIG. 1, as described herein. The first outlet portion 23 of the connector 22 is also in fluid communication with the second drainage tube 14 to transfer blood from the second drainage tube 14 to the blood pump in the direction of the arrow shown in FIG. 1, as described herein. The first outlet portion 23 is in fluid communication with the first and second outlet portions 24, 26 which are arranged such that the fluid pathways leading from the first and second drainage tubes 12, 14 transition from a coaxial arrangement at a distal end of the connector 22 to an axially-offset arrangement at a proximal end of the connector 22. Connector 22 restricts blood flow path to a streamlined consistent path to avoid hemolysis and stagnation in flow. In some aspects, the first and second outlet portions 24, 26 may have barbed fittings for connecting to additional tubing that leads to the blood pump (shown in FIG. 9).

Figure 3:
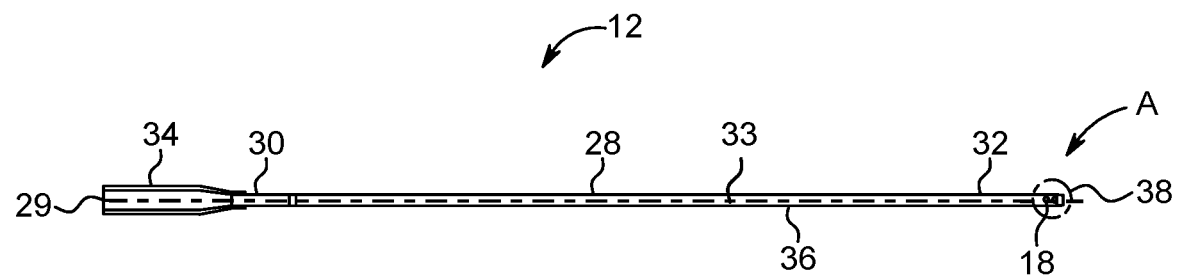
FIG. 3 is a top view of one aspect of an infusion cannula.
Figure 4:
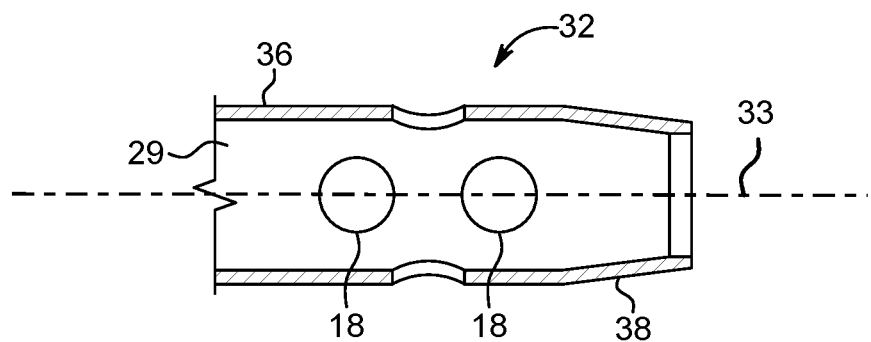
FIG. 4 is a cross-sectional view of detail A shown in FIG. 3.

With reference to FIGS. 3-4, and with continuing reference to FIGS. 1-2, the first drainage tube 12 is illustrated separate from the drainage cannula 10. The first drainage tube 12 has a first elongate body 28 having a substantially cylindrical shape and extending from a first proximal end 30 to a first distal end 32 of the first drainage tube 12. The first elongate body 28 includes a first lumen 29 extending throughout the entire length of the first drainage tube 12. The first proximal end 30 includes a first connector portion 34 for coupling the first drainage tube 12 to the first outlet portion 23 of the connector 22 (shown in FIG. 1). The first elongate body 28 of the first drainage tube 12 has a hollow structure defined by a first sidewall 36 extending circumferentially about the first elongate body 28. The first sidewall 36 has a substantially constant thickness throughout the length of the first elongate body 28, with a first tapering section 38 at the first distal end 32 of the first elongate body 28. At the first proximal end 30 of the first elongate body 28, the first sidewall 36 gradually increases in thickness before transitioning into the first connector portion 34, which is done with a streamlined blood flow path to avoid hemolysis or flow stagnation. The first tapering section 38 located at the first distal end 32 has a thinner first sidewall 36 but retains the internal diameter of the first drainage tube 12. The first tapering section 38 enables easier insertion of the first drainage tube 12 into the patient's body.

With specific reference to FIG. 4, the first distal end 32 of the first drainage tube 12 is shown. The plurality of first drainage apertures 18 is provided at the first distal end 32 of the first drainage tube 12. The plurality of first drainage apertures 18 extends circumferentially around the first distal end 32. Each first drainage aperture 18 has a diameter of, for example, about 0.094+/−0.010 in. The plurality of first drainage apertures 18 may be arranged in an alternating pattern of axially offset rows of first drainage apertures 18 arranged around the circumference of the first drainage tube 12. Each of the plurality of first drainage apertures 18 extends through the thickness of the first sidewall 36. In one aspect, six first drainage apertures 18 may be provided on the first drainage tube 12. The first drainage apertures 18 illustrated in FIGS. 3-4 extend through the first sidewall 36 in a direction perpendicular to a longitudinal axis of the first elongate body 28. Alternatively, the plurality of first drainage apertures 18 may extend through the thickness of the first sidewall 36 in an angled manner with respect to the longitudinal axis of the first elongate body 28. For example, the plurality of first drainage apertures 18 may be arranged at an acute or obtuse angle with respect to a cross-sectional plane of the first drainage tube 12 and extend perpendicular to the longitudinal axis of the first elongate body 28. In one aspect, one or more sensors (not shown) may be provided at the first distal end 32 of the first drainage tube 12. The sensor(s) may be adapted for measuring, for example, local blood pressure and/or oxygen concentration. At least a portion of the first drainage tube 12 may be reinforced, such as with a wire at least partially embedded with the first drainage tube 12. In addition, at least a portion of the first drainage tube 12 may have one or more indicia, such as a radiopaque marker, visible under fluoroscopy or cine-angiography to assist with positioning of the first drainage tube 12 within the patient's vasculature.

The total cross-sectional area of the plurality of first drainage apertures 18 is desirably approximately equal to or greater than the cross-sectional area of the first lumen 29. If the cross-sectional area of the plurality of first drainage apertures 18 is less than the cross-sectional area of the first lumen 29, an undesirable pressure drop may occur. This pressure drop reduces the flow throughput within the first lumen 29 and impairs the efficiency of the first drainage tube 12. Desirably, the total cross-sectional area of the plurality of first drainage apertures 18 exceeds the cross-sectional area of the first lumen 29 such that if one or more of the first drainage apertures 18 becomes clogged, the total cross-sectional area of the remaining first drainage apertures 18 is equal to or greater than the cross-sectional area of the first lumen 29. In this manner, the blood flow through the first lumen 29 is maximized even if one or more of the first drainage apertures 18 become clogged. The first drainage tube 12 is configured for placement within the patient's vasculature such that the plurality of first drainage apertures 18 provided at the first distal end 32 of the first drainage tube 12 are positioned within the right atrium of the patient's heart.

Figure 5:
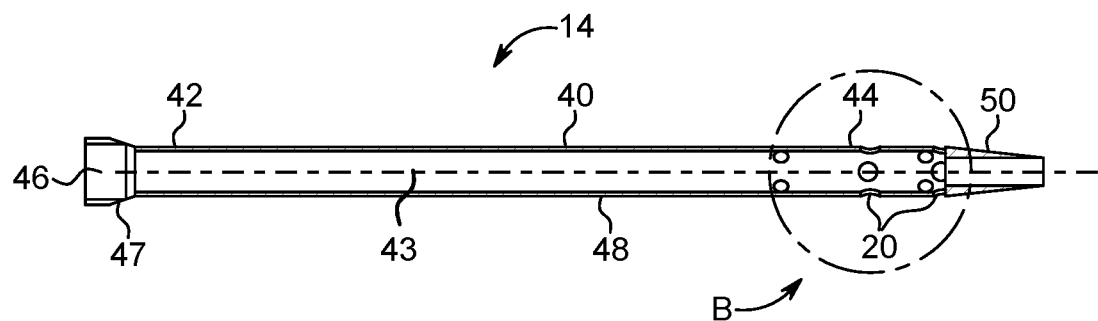
FIG. 5 is a top view of one aspect of a drainage cannula.
Figure 6:
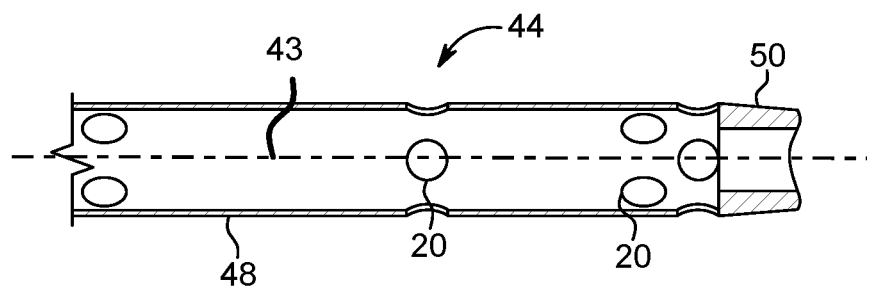
FIG. 6 is a cross-sectional view of detail B in FIG. 5.

With reference to FIGS. 5-6, and with continuing reference to FIGS. 1-2, the second drainage tube 14 is illustrated separate from the drainage cannula 10. The second drainage tube 14 has a second elongate body 40 having a substantially cylindrical shape and extending from a second proximal end 42 to a second distal end 44 of the second drainage tube 14. The second elongate body 40 includes a second lumen 46 extending throughout the entire length of the second drainage tube 14. The second proximal end 42 includes a second connector portion 47 for coupling the second drainage tube 14 to the first outlet portion 24 of the connector 22 (shown in FIG. 1). The second elongate body 40 of the second drainage tube 14 has a hollow structure defined by a second sidewall 48 extending circumferentially about the second elongate body 40. The second sidewall 48 has a substantially constant thickness throughout the length of the second elongate body 40, with a second tapering section 50 at the second distal end 44 of the second elongate body 40. At the second proximal end 42 of the second elongate body 40, the second sidewall 48 gradually increases in thickness before transitioning into the second connector portion 47. The second tapering section 50 located at the second distal end 44 has a thinner second sidewall 48 but retains the internal diameter of the second lumen 46. The second tapering section 50 enables easier insertion of the second drainage tube 14 into the patient's body.

With specific reference to FIG. 6, the second distal end 44 of the second drainage tube 14 is shown. The plurality of second drainage apertures 20 is provided at the second distal end 44 of the second drainage tube 14. The plurality of second drainage apertures 20 extends circumferentially around the second distal end 44. Each second drainage aperture 20 has a diameter of, for example, about 0.120 in.+/−0.010 in. The plurality of second drainage apertures 20 may be arranged in an alternating pattern of axially offset rows around the circumference of the second drainage tube 14. Each of the plurality of second drainage apertures 20 extends through the thickness of the second sidewall 48. In one aspect, eighteen second drainage apertures 20 are provided on the second drainage tube 14. The second drainage apertures 20 illustrated in FIGS. 5-6 extend through the second sidewall 48 in a direction perpendicular to a longitudinal axis of the second elongate body 40. Alternatively, the plurality of second drainage apertures 20 may extend through the thickness of the second sidewall 48 in an angled manner with respect to the longitudinal axis of the second elongate body 40. For example, the plurality of second drainage apertures 20 may be arranged at an acute or obtuse angle with respect to a cross-sectional plane of the second drainage tube 14 and extend perpendicular to the longitudinal axis of the second elongate body 40. In one aspect, one or more sensors (not shown) may be provided at the second distal end 44 of the second drainage tube 14. The sensor(s) may be adapted for measuring, for example, local blood pressure and/or oxygen concentration. At least a portion of the second drainage tube 14 may be reinforced, such as with a wire at least partially embedded with the second drainage tube 14. In addition, at least a portion of the second drainage tube 14 may have one or more indicia, such as a radiopaque marker, visible under fluoroscopy or cineangiography to assist with positioning of the second drainage tube 14 within the patient's vasculature.

The total cross-sectional area of the plurality of second drainage apertures 20 is desirably approximately equal to or greater than the cross-sectional area of the second lumen 46. If the cross-sectional area of the plurality of the second drainage apertures 20 is less than the cross-sectional area of the second lumen 46, an undesirable pressure drop within the second drainage tube 14 may occur. This pressure drop reduces the flow throughput within the second lumen 46 and impairs the efficiency of the second drainage tube 14. Desirably, the total cross-sectional area of the plurality of second drainage apertures 20 exceeds the cross-sectional area of the second lumen 46 such that if one or more second drainage apertures 20 becomes clogged, the total cross-sectional area of the remaining second drainage apertures 20 is equal to or greater than the cross-sectional area of the second lumen 46. In this manner, the blood flow through the second lumen 46 is maximized even if one or more of the second drainage apertures 20 becomes clogged. The second drainage tube 14 is configured for placement within the patient's vasculature such that the plurality of second drainage apertures 20 provided at the second distal end 44 of the first drainage tube 12 are positioned within the pulmonary artery of the patient's heart.

Figure 7:
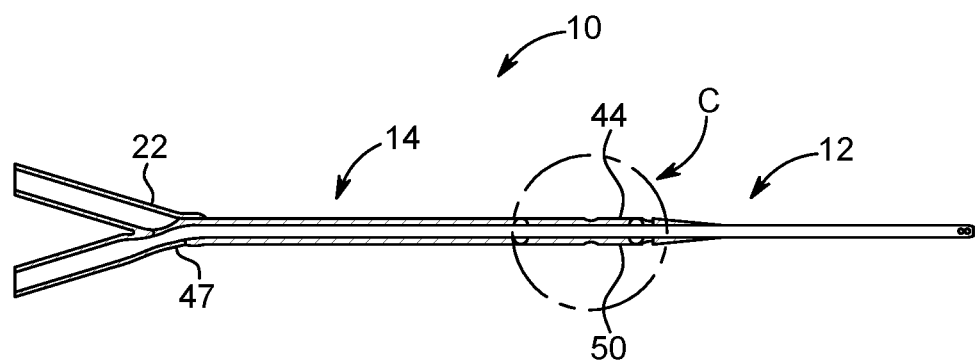
FIG. 7 is a top cross-sectional view of the drainage cannula taken along line A-A in FIG. 2.
Figure 8:
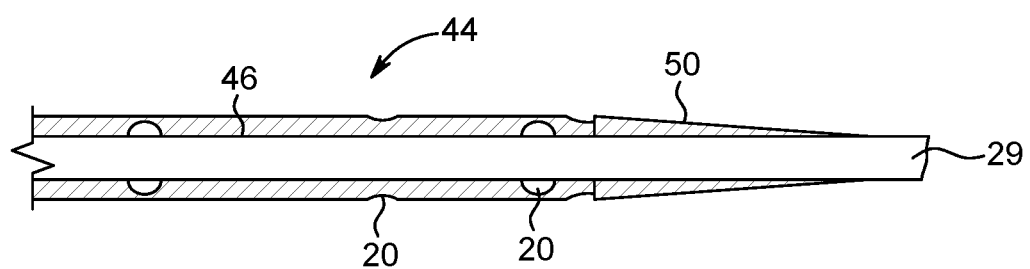
FIG. 8 is a cross-sectional view of detail C in FIG. 7, illustrating a transition portion at a distal end of the drainage cannula.

With reference to FIG. 7, the drainage cannula 10 shown in FIGS. 1-2 is illustrated in cross-section. The second distal end 44 of the second drainage tube 14 is fixedly attached to the first drainage tube 12 along the length of the second tapering section 50, as shown in FIG. 8. The first drainage tube 12 and the second drainage tube 14 are coupled to the connector 22 in such a manner that the first drainage tube 12 and the second drainage tube 14 cross inside the connector 22 body without being connected to each other.

Figure 9:
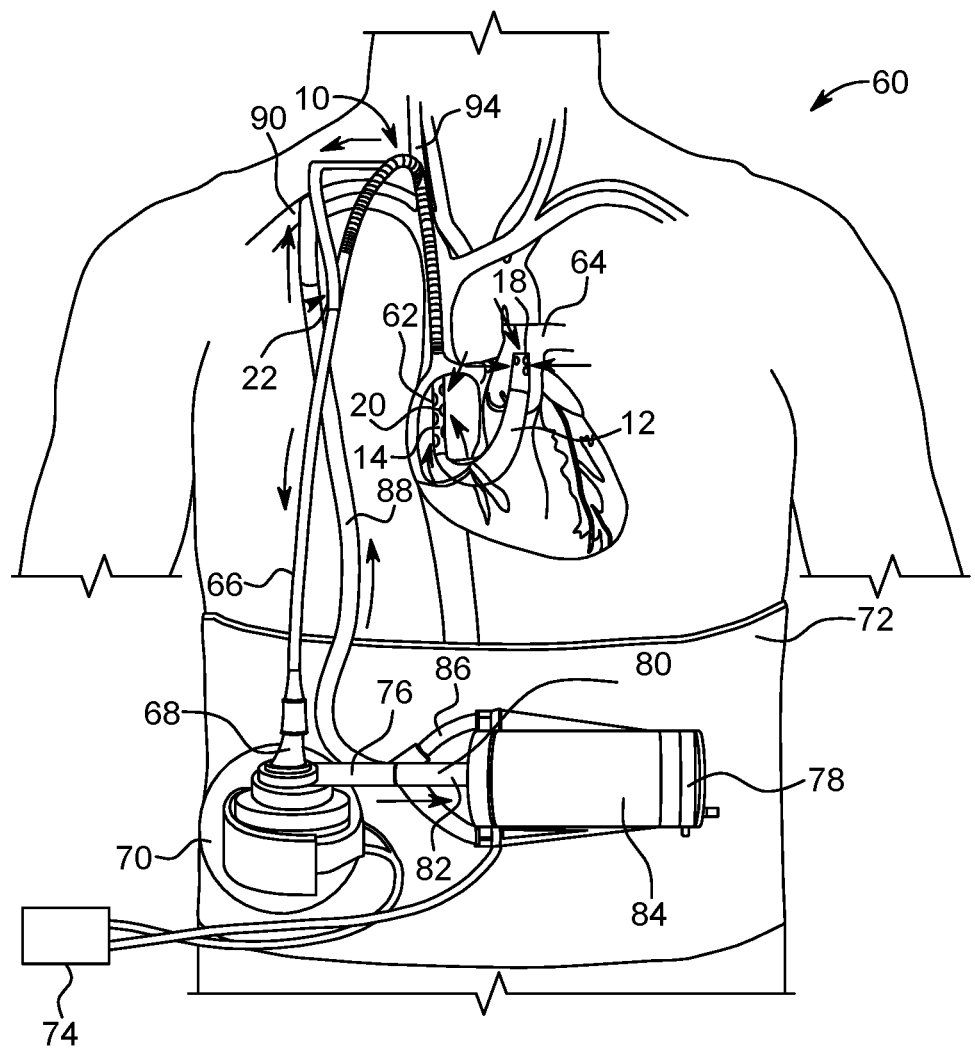
FIG. 9 is an illustration of a VA ECMO system in accordance with one aspect.

With reference to FIG. 9, a VA ECMO system 60 having the drainage cannula 10 is illustrated in accordance with one aspect. The VA ECMO system 60 includes the drainage cannula 10 having the first drainage tube 12 configured for positioning within the right atrium 64 and the second drainage tube 14 configured for positioning within the patient's pulmonary artery 62. The first and second drainage tubes 12, 14 are positioned within the right atrium 64 and the pulmonary artery 62, respectively, such that blood may enter the respective lumens 29, 46 (shown in FIG. 8) of the first and second drainage tubes 12, 14 through the plurality of first and second drainage apertures 18, 20, respectively.

Figure 12:
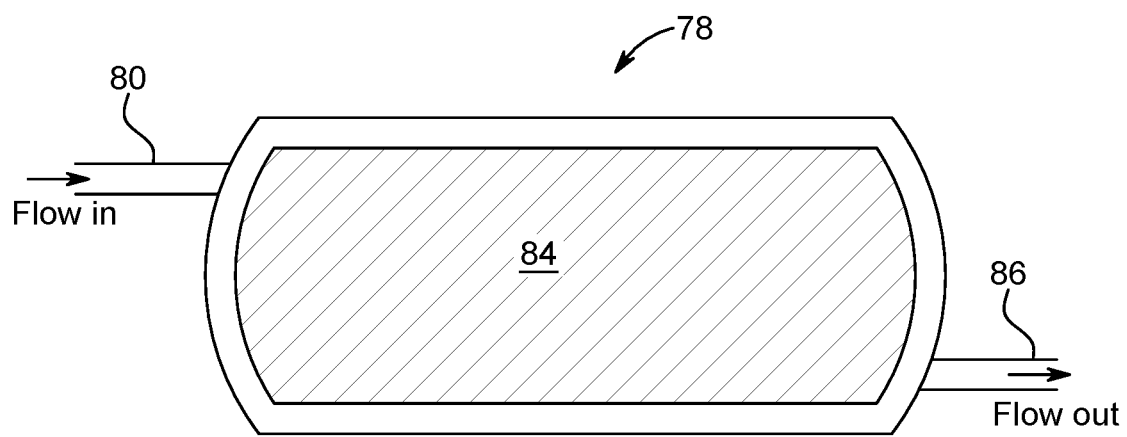
FIG. 12 is a side view of an oxygenator for use with a VA ECMO system.

The connector 22 of the drainage cannula 10 may be connected to an inlet conduit 66 that delivers blood to an inlet 68 of a pump 70. In some aspects, the connector 22 may be directly connected to the inlet 68 of the pump 70. The pump 70 can be any centrifugal, axial, mixed, or roller pump that can produce adequate flowrates through the system. Several examples of pumps include, without limitation the TANDEMHEART pump manufactured by Cardiac Assist, Inc., the BIOMEDICUS pump manufactured by Medtronic, Inc., the ROTAFLOW pump manufactured by Jostra Medizintechnik AG, the CENTRIMAG pump manufactured by Levitronix, LLC, the SARNS DELPHIN pump manufactured by the Terumo Cardiovascular Group, the REVOLUTION pump manufactured by Cobe Cardiovascular, Inc, and others. The pump 70 can be secured to the patient, for instance with a holster 72 that holds the pump 70 with a strap or in a pocket. The holster 72 can be wrapped around the abdomen or shoulder or leg of the patient. A controller 74 may be provided for controlling the operation of the pump 70. The controller 74 may be built into the pump 70. The pump 70 further includes an outlet 76 for delivering blood to an oxygenator 78 at an oxygenator inlet 80. The oxygenator 78 may be secured to the holster 72. The pump outlet 76 may be directly connected to the oxygenator inlet 80. In some aspects, the pump outlet 76 may be connected to the oxygenator inlet 80 via an outlet conduit 82. With reference to FIG. 12, the oxygenator 78 includes an oxygenation membrane 84 or other element(s) for oxygenating blood flowing from the oxygenator inlet 80 to an oxygenator outlet 86. Oxygenated blood is delivered to an artery in the patient's body through an infusion cannula 88 (shown in FIG. 9). While FIG. 9 illustrates the infusion cannula 88 connected to the patient's subclavian artery 90, in other aspects, the infusion cannula 88 may be connected to the patient's femoral artery 92 (shown in FIG. 10), subclavian artery, or other artery of the patient's vascular system.

One advantage of using the drainage cannula 10 is that the drainage cannula 10 allows the right atrial sourcing site to drain the majority of venous flow, such as 4 liters per minute (lpm) (out of a typical system flow of 5 lpm), leaving the pulmonary artery lumen to drain the remaining 1 lpm. Without the drainage cannula 10, two separate cannula would be required as a single cannula in the pulmonary artery is insufficient to completely drain the full 5 lpm of venous flow. The drainage cannula 10 drains blood from the pulmonary artery and the right atrium in addition to any residual blood in the left atrium, thereby reducing left atrial pressure and thus preventing additional load on the heart, or resulting in VA ECMO with an unloaded left ventricle. Blood is drawn from two sites within the patient's heart through a single insertion site, pumped through an oxygenator and delivered back into the arterial circulation via a separate, infusion cannula 88 into the femoral artery, the subclavian artery, or other artery of the patient's vascular system.

In accordance with some aspects, a single lumen cannula (not shown) having at least two axially offset drainage apertures may be used to draw blood from the right atrium and separately from the pulmonary artery, which, through minimal loss of pressure across the lung bed, will also drain the left atrium. At least one expandable balloon may be provided between the drainage apertures to prevent blood flow between the apertures.

Having described several non-limiting aspects of the drainage cannula 10 and the VA ECMO system 60, an exemplary and non-limiting method for bilateral unloading of a patient's heart using the drainage cannula 10 will now be described with reference to FIGS. 9-10. Prior to the initial use, the package (not shown) containing the drainage cannula 10 is inspected for damage and expiration date. If undamaged and within the expiration date, the drainage cannula 10 is transferred to a sterile field using an aseptic technique.

In use, the drainage cannula 10 is inserted into the patient's vasculature in a percutaneous procedure prior to being connected to an ECMO system. Initially, a percutaneous entry needle (not shown) is used to access the patient's internal jugular vein 94 (FIGS. 9-10) or the femoral vein 96 (FIG. 11). A guidewire, such as a guidewire having maximum diameter 0.038 in. (0.965 mm) and a minimum length of 170 cm, is inserted into the vasculature. In some aspects, the positioning of the guidewire is verified using an appropriate imaging technique. In the next step, the patient's active clotting time is checked for approximately 400 seconds.

In the next step, the drainage cannula 10 is prepared for insertion into the patient's vasculature. The drainage cannula 10 is initially assembled by removing an introducer with a hemostasis cap from its protective sheath (not shown). After flushing the introducer with a saline solution to verify that the distal tip of the introducer is not obstructed, the introducer is inserted into the first drainage tube 12 until the hemostasis cap seats securely on the first connector portion 34. The hemostasis cap is then secured to the second drainage tube 14. In some aspects, first and second drainage tubes 12, 14 may have indicia, such as the words "Distal" and "Proximal", respectively, to assist the medical practitioner in placing the introducer and the hemostasis cap into the correct drainage tube. The introducer/drainage cannula assembly may then be guided over the guidewire into the desired position within the patient's vasculature.

In particular, introducer/drainage cannula assembly is advanced over the guidewire until the assembly reaches the desired position. In some aspects, the introducer/drainage cannula assembly may be guided into a desired position using the indicia, such as a radiopaque marker located in the first distal end 32 of the first drainage tube 12, that is visualized under fluoroscopy, transthoracic echocardiography, or cineangiography. The position of the introducer/drainage cannula assembly may be guided and verified by an imaging system described in WO 2015/139031. In some aspects, the first drainage apertures 18 on the first drainage tube 12 may be placed in the right atrium, while the second drainage apertures 20 on the second drainage tube 14 may be placed within the pulmonary artery. After noting and recording the location of the drainage cannula 10, the introducer can be removed, leaving the hemostasis cap on the drainage cannula 10 to minimize blood loss. The drainage cannula 10 can be clamped at a clamping zone indicated on first drainage tube 12 as the introducer is removed. The hemostasis cap can then be removed from the second drainage tube 14.

To connect the drainage cannula 10 to the blood pump 70, a wet-to-wet, or other type, of a connection is made between the drainage cannula 10 and tubing that is attached to the pump 70. Both tubes of the drainage cannula 10 should be connected to the connector 22 and the inlet of the pump 70, and the drainage cannula 10 should not be kinked. After verifying the correct positioning and insertion depth of the drainage cannula 10, the drainage cannula 10 can be secured to the patient, such as by suturing with a suture wing. The patient's active clotting time is checked for approximately 180-220 seconds before turning on the blood pump 70 to circulate the patient's blood through the system. During use, the blood pump 70 pumps the blood withdrawn through the first and second drainage tubes 12, 14 through the oxygenator 78 to oxygenate the blood, which is then returned to the patient via the infusion line 86. After use, the pump 70 is turned off and the pump inlet and outlet are clamped. The tubing is cut and the pump 70 may be removed. Any sutures securing the drainage cannula 10 to the patient may be removed, and the drainage cannula 10 removed from the patient. The puncture site may then be treated and dressed.

Although the disclosure has been described in detail for the purpose of illustration based on what is currently considered to be the most practical and preferred aspects, it is to be understood that such detail is solely for that purpose and that the disclosure is not limited to the disclosed aspects, but, on the contrary, is intended to cover modifications and equivalent arrangements. For example, it is to be understood that the present disclosure contemplates that, to the extent possible, one or more features of any aspect can be combined with one or more features of any other aspect.

The invention claimed is:

1. A veno-arterial extracorporeal membrane oxygenation (VA ECMO) system comprising:
   a dual lumen drainage cannula comprising:
      a first drainage tube configured for fluid drainage from a first portion of a cardiopulmonary system; and
      a second drainage tube aligned with the first drainage tube and configured for fluid drainage from a second portion of the cardiopulmonary system;
   a blood pump having a pump inlet and a pump outlet, the pump inlet configured for fluidly connecting with the first drainage tube and the second drainage tube;
   an oxygenator having an oxygenator inlet and an oxygenator outlet, the oxygenator inlet configured for fluidly connecting with the pump outlet; and
   an infusion cannula configured for fluidly connecting with the oxygenator outlet;
   wherein a distal end of the second drainage tube is fixedly connected to the first drainage tube.

2. The VA ECMO system of claim 1, wherein the distal end of the second drainage tube comprises a tapering section and wherein the second drainage tube is fixedly connected to the first drainage tube along a length of the tapering section.

3. The VA ECMO system of claim 1, wherein the first drainage tube and the second drainage tube are coaxially aligned.

4. The VA ECMO system of claim 1, further comprising a connector having a first end configured for fluidly connecting with a proximal end of the first drainage tube and a proximal end of the second drainage tube.

5. The VA ECMO system of claim 4, wherein a second end of the connector is configured for fluidly connecting with the pump inlet.

6. The VA ECMO system of claim 1, wherein the first drainage tube has at least one first drainage aperture at a distal end thereof.

7. The VA ECMO system of claim 6, wherein the at least one first drainage aperture extends through a sidewall of the first drainage tube in a direction perpendicular to a longitudinal axis of the first drainage tube.

8. The VA ECMO system of claim 6, wherein the at least one first drainage aperture extends through a sidewall of the first drainage tube at an acute angle or an obtuse angle relative to a longitudinal axis of the first drainage tube.

9. The VA ECMO system of claim 6, wherein the at least one first drainage aperture is a plurality of first drainage apertures extending around the first drainage tube.

10. The VA ECMO system of claim 1, wherein the second drainage tube has at least one second drainage aperture at the distal end thereof.

11. The VA ECMO system of claim 10, wherein the at least one second drainage aperture extends through a sidewall of the second drainage tube in a direction perpendicular to a longitudinal axis of the second drainage tube.

12. The VA ECMO system of claim 10, wherein the at least one second drainage aperture extends through a sidewall of the second drainage tube at an acute angle or an obtuse angle relative to a longitudinal axis of the second drainage tube.

13. The VA ECMO system of claim 10, wherein the at least one second drainage aperture is a plurality of second drainage apertures extending around the second drainage tube.

14. The VA ECMO system of claim 1, wherein the dual lumen cannula is configured for maneuvering through the cardiopulmonary system such that a distal end of the first drainage tube is positioned substantially within a right atrium of a heart and such that the distal end of the second drainage tube is positioned substantially within a pulmonary artery of the heart.

15. A method of providing veno-arterial extracorporeal membrane oxygenation of a heart, the method comprising:
   providing a dual lumen drainage cannula comprising:
      a first drainage tube configured for fluid drainage from a first portion of a cardiopulmonary system; and
      a second drainage tube aligned with the first drainage tube and configured for fluid drainage from a second portion of the cardiopulmonary system,
         wherein a distal end of the second drainage tube is fixedly connected to the first drainage tube;
   inserting the dual lumen drainage cannula into a first site in a vasculature of a patient such that a distal end of the first drainage tube is positioned substantially within a right atrium of a heart and such that the distal end of the second drainage tube is positioned substantially within a pulmonary artery of the heart;
   withdrawing blood through the first drainage tube and the second drainage tube using a blood pump;
   pumping withdrawn blood through an oxygenator; and
   delivering oxygenated blood to a second site in the vasculature.

* * * * *